(12) United States Patent
Koulik

(10) Patent No.: US 6,630,460 B2
(45) Date of Patent: *Oct. 7, 2003

(54) HEPARIN COMPOSITIONS AND METHODS OF MAKING AND USING THE SAME

(75) Inventor: Edouard Koulik, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 81 days.

This patent is subject to a terminal disclaimer.

(21) Appl. No.: 09/779,536

(22) Filed: Feb. 9, 2001

(65) Prior Publication Data

US 2002/0150670 A1 Oct. 17, 2002

(51) Int. Cl.[7] .................. A61K 31/725; C08B 37/10
(52) U.S. Cl. .................. 514/56; 536/21; 536/124; 623/11
(58) Field of Search .................. 514/56; 536/21, 536/124; 623/11

(56) References Cited

U.S. PATENT DOCUMENTS

| | | |
|---|---|---|
| 3,846,353 A | 11/1974 | Grotta |
| 4,331,697 A | 5/1982 | Kudo et al. |
| 4,529,614 A | 7/1985 | Burns |
| 4,600,652 A | 7/1986 | Solomon et al. |
| 4,613,665 A | 9/1986 | Larm |
| 4,642,242 A | 2/1987 | Solomon et al. |
| 4,678,660 A | 7/1987 | McGary et al. |
| 4,720,512 A | 1/1988 | Hu et al. |
| 4,786,556 A | 11/1988 | Hu et al. |
| 5,032,666 A | 7/1991 | Hu et al. |
| 5,061,738 A | 10/1991 | Solomon et al. |
| 5,077,372 A | 12/1991 | Hu et al. |
| 5,270,046 A | 12/1993 | Sakamoto et al. |
| 5,356,433 A | 10/1994 | Rowland et al. |
| 5,441,759 A | 8/1995 | Crouther et al. |
| 5,447,724 A | 9/1995 | Helmus et al. |
| 5,455,040 A | 10/1995 | Marchant |
| 5,541,167 A | 7/1996 | Hsu et al. |
| 5,569,463 A | 10/1996 | Helmus et al. |
| 5,607,475 A * | 3/1997 | Cahalan et al. ............. 623/11 |
| 5,616,338 A | 4/1997 | Fox, Jr. et al. |
| 5,679,659 A * | 10/1997 | Verhoeven et al. ........... 514/56 |
| 5,741,551 A | 4/1998 | Guire et al. |
| 5,782,908 A * | 7/1998 | Cahalan et al. ............. 623/1 |
| 5,879,697 A | 3/1999 | Ding et al. |
| 5,945,457 A | 8/1999 | Plate et al. |
| 5,951,586 A | 9/1999 | Berg et al. |
| 6,024,918 A | 2/2000 | Hendriks et al. |
| 6,096,726 A | 8/2000 | Opolski |
| 6,110,483 A | 8/2000 | Whitbourne et al. |
| 6,143,354 A | 11/2000 | Koulik et al. |
| 2002/0068183 A1 * | 6/2002 | Huang et al. ............. 428/474.4 |

* cited by examiner

Primary Examiner—James O. Wilson
Assistant Examiner—Devesh Khare
(74) Attorney, Agent, or Firm—Thomas F. Woods; Eric R. Waldkoetter; Tom G. Berry

(57) ABSTRACT

Heparin-polyoxyalkylenepolyamine adducts, and methods of making and using such adducts are disclosed. Compositions including a quaternary ammonium heparin complex, a moisture curable polysiloxane, and an organic solvent are also disclosed, along with methods of making and using such compositions.

10 Claims, 1 Drawing Sheet

HEPARIN COMPOSITIONS AND METHODS OF MAKING AND USING THE SAME

FIELD OF THE INVENTION

The present invention relates to heparin compositions, methods of making such compositions, and compositions prepared therefrom.

BACKGROUND

Development of materials that do not induce hostile response from the body tissues upon implantation or insertion in a human or animal body is an important target in the medical device field. In practice, many commonly used materials including plastics, ceramics, and metals have substantial biocompatibility problems.

One important property for medical devices that contact blood after implantation or insertion in a human or animal body is thrombogenicity. Thrombogenicity is the ability of the device to induce formation of blood clots. For blood to clot, it is believed that thrombin must be generated in the blood. Several potent anticoagulants are known that are able to prevent formation of thrombin. The most widely used anticoagulant used during surgical procedures is heparin. When heparin is immobilized on the surface of a medical device, the ability of the surface to induce formation of clots decreases, or in other words, the surface becomes antithrombogenic. However, the antithrombogenicity of a heparinized surface tends to decrease as the surface heparin loses its potency to retard clot formation. Many heparinized surfaces tend to have poor stability in vivo. New heparin compositions and coatings are needed to improve the antithrombogenic stability of heparinized surfaces.

A few reports of heparin compositions and methods of making and using heparin and antithrombogenic compositions have appeared in the art, some examples of which may be found in the patents and publications listed in Table 1 below.

TABLE 1

Patents and Publications

| Patent/Publication No. | Inventor(s) | Issue/Publication Date |
|---|---|---|
| U.S. Pat. No. 6,143,354 | Koulik et al. | 7 Nov. 2000 |
| U.S. Pat. No. 6,110,483 | Whitbourne et al. | 29 Aug. 2000 |
| U.S. Pat. No. 6,096,726 | Opolski | 1 Aug. 2000 |
| U.S. Pat. No. 6,024,918 | Hendriks et al. | 15 Feb. 2000 |
| U.S. Pat. No. 5,951,586 | Berg et al. | 14 Sep. 1999 |
| U.S. Pat. No. 5,945,457 | Plate et al. | 31 Aug. 1999 |
| U.S. Pat. No. 5,879,697 | Ding et al. | 9 Mar. 1999 |
| U.S. Pat. No. 5,782,908 | Cahalan et al. | 21 Jul. 1998 |
| U.S. Pat. No. 5,741,551 | Guire et al. | 21 Apr. 1998 |
| U.S. Pat. No. 5,616,338 | Fox, Jr. et al. | 1 Apr. 1997 |
| U.S. Pat. No. 5,607,475 | Cahalan et al. | 4 Mar. 1997 |
| U.S. Pat. No. 5,569,463 | Helmus et al. | 29 Oct. 1996 |
| U.S. Pat. No. 5,541,167 | Hsu et al. | 30 Jul. 1996 |
| U.S. Pat. No. 5,455,040 | Marchant | 3 Oct. 1995 |
| U.S. Pat. No. 5,447,724 | Helmus et al. | 5 Sep. 1995 |
| U.S. Pat. No. 5,441,759 | Crouther et al. | 15 Aug. 1995 |
| U.S. Pat. No. 5,356,433 | Rowland et al. | 18 Oct. 1994 |
| U.S. Pat. No. 5,270,046 | Sakamoto et al. | 14 Dec. 1993 |
| U.S. Pat. No. 5,077,372 | Hu et al. | 31 Dec. 1991 |
| U.S. Pat. No. 5,061,738 | Solomon et al. | 29 Oct. 1991 |
| U.S. Pat. No. 5,032,666 | Hu et al. | 16 Jul. 1991 |
| U.S. Pat. No. 4,786,556 | Hu et al. | 22 Nov. 1988 |
| U.S. Pat. No. 4,720,512 | Hu et al. | 19 Jan. 1988 |
| U.S. Pat. No. 4,678,660 | McGary et al. | 7 Jul. 1987 |
| U.S. Pat. No. 4,642,242 | Solomon et al. | 10 Feb. 1987 |
| U.S. Pat. No. 4,613,665 | Larm | 23 Sep. 1986 |
| U.S. Pat. No. 4,600,652 | Solomon et al. | 15 Jul. 1986 |
| U.S. Pat. No. 4,529,614 | Burns | 16 Jul. 1985 |
| U.S. Pat. No. 4,331,697 | Kudo et at. | 25 May 1982 |
| U.S. Pat. No. 3,846,353 | Grotta | 5 Nov. 1974 |

Technical Publications
Dow Corning MDX4-4159 Fluid 50% Medical Grade Dispersion, Product Information Sheet, Copyright 2000

All patents and publications listed in Table 1 above are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the patents and publications of Table 1 may be modified advantageously by using the teachings of the present invention.

SUMMARY OF THE INVENTION

The present invention has certain objects. That is, various embodiments of the present invention provide solutions to one or more problems existing in the prior art respecting heparin compositions and methods and making and using such compositions. Those problems include heparin compositions having poor solubility in organic solvents, heparin compositions having poor antithrombogenic stability, heparin compositions having poor adhesion to surfaces, heparin compositions requiring special surface treatments that may result in degradation of surface properties, heparin compositions having limited antithrombogenicity, heparin compositions having high release rates upon exposure to body fluids, heparin compositions having low release rates upon exposure to body fluids, heparin compositions with inadequate mechanical properties, heparin compositions requiring thermal treatments, heparin compositions requiring thick coating layers, and heparin compositions requiring the used of toxic chemical compounds. Various embodiments of the present invention have the object of solving at least one of the foregoing problems. While some conventional heparin compositions were capable of solving at least some of the foregoing problems, they were generally not employed because of their prohibitively high cost or difficult production processes. It is therefore another object of the present invention to provide improved heparin compositions that may be produced, used, and sold at low cost, yet still fulfill at least one of the foregoing objects.

In comparison to known heparin compositions and methods of making and using such compositions, various embodiments of the present invention may provide one or more of the following advantages. The present invention provides heparin compositions with improved properties over heparin compositions known in the art. For example, heparin compositions of the present invention are preferably soluble in organic solvents. Preferably the heparin compositions of the present invention have a solubility in isopropyl alcohol at room temperature of at least about 1% by weight, and more preferably, at least about 5% by weight. Organic solubility may be important in preventing complications including undue limitations in formulating coating fluids, difficult or inefficient coating processes, inadequate coating uniformity, and low quantity of attached or imbedded heparin. Heparin compositions of the present invention also preferably provide coating compositions with adequate adhesion to the surface of a device, preferably a medical device. Heparinized surfaces that include heparin compositions of the present invention preferably maintain antithrombogenicity after several hours under high blood flow in vivo conditions, for example, in a heart or an aorta. Preferably, heparinized surfaces that include heparin compositions of the present invention provide excellent mechanical properties and suitable electrical properties in applications including, for example, medical devices.

The present invention also provides advantageous methods for preparing heparinized surfaces. Surfaces that include heparin compositions of the present invention preferably provide sustained release of heparin upon exposure to body fluids. Methods of the present invention also allow the preparation of coating compositions that include organic soluble heparin-adducts and/or heparin complexes. Such coating compositions allow the use of coating processes that may provide economic advantages as well as product quality improvements. For example, dip-coating or spray-coating methods of the present invention preferably provide uniform coating layers. Coating uniformity may be desirable for sustained release of heparin upon exposure to body fluids.

Definitions

As used herein, "adduct" means a covalently bonded reaction product of two named chemical species. For example, a heparin-polyoxyalkylenepolyamine adduct is a covalently bonded reaction product formed by the reaction of a heparin species with a polyoxyalkylenepolyamine.

As used herein, "complex" means an ionically bonded reaction product of a cationic species and an anionic species. For example, a quaternary ammonium heparin complex is an ionically bonded reaction product formed by the reaction of a cationic quaternary ammonium species with an anionic heparin species.

As used herein, "organic soluble" refers to solubility in typical organic solvents including, for example, tetrahydrofuran, acetone, ethanol, isopropanol, methylene chloride, chloroform, hexane, heptane, xylenes, toluene, dioxolane, and N,N-dimethylacetamide. The organic solvent preferably does not include substantial amounts of water. The organic solvent may include at most about 10% by weight water and preferably at most about 5% by weight water. An organic soluble composition has solubility of at least about 1% by weight in isopropyl alcohol at room temperature. Preferably, an organic soluble composition has solubility of at least about 5% by weight in isopropyl alcohol at room temperature.

As used herein, "water insoluble" means that the composition does not have substantial solubility in water. A substantially water insoluble composition has solubility of at most about 2% by weight in water at room temperature. Preferably, a substantially water insoluble composition has solubility of at most about 0.1% by weight in water at room temperature.

As used herein, "uniform coating" means that the surface is completely covered by the coating.

As used herein, "moisture curable" means that curing may be initiated upon exposure to moisture (i.e., water), in either the liquid or the vapor state.

As used herein, the term "curing" includes hardening, crosslinking, polymerizing, chain extending, and other related chemical reactions. Preferably a cured material has undergone sufficient hardening, crosslinking, polymerizing, or chain extending to provide a material in the solid state.

As used herein, "heparin" refers to a heterogeneous group of straight-chain anionic mucopolysaccharides having anticoagulant properties.

DETAILED DESCRIPTION OF THE PREFERRED EMBODIMENTS

Figure 1:
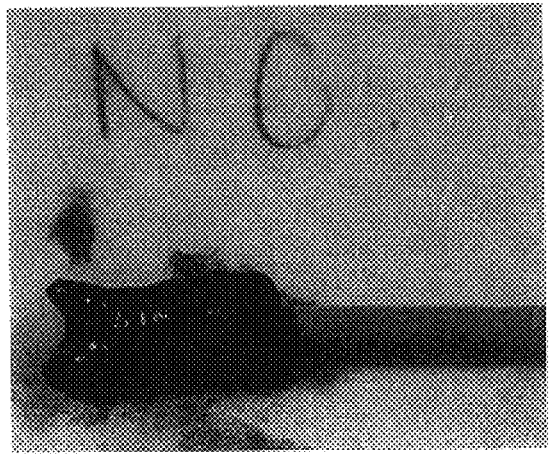
FIG. 1 is a photograph of an uncoated catheter after being exposed to blood for 30 minutes, followed by rinsing with Plasma-Lyte A.

In one aspect, the present invention provides heparin-polyoxyalkylenepolyamine adducts, which preferably are organic soluble. Preferably the adducts are quaternary ammonium complexes. Preferably the adducts are preparable by reacting periodate heparin with a polyoxyalkylenepolyamine.

In another aspect, the present invention provides a composition that includes a heparin-polyoxyalkylenepolyamine adduct and an organic solvent. Preferably the adduct is organic soluble. Preferably the composition further including a polysiloxane.

In another aspect, the present invention provides an object having a coating layer, wherein the coating layer includes a heparin-polyoxyalkylenepolyamine adduct. Preferably the coating layer further includes a polysiloxane. Preferably the object is a medical device.

In another aspect, the present invention provides a method for preparing a heparin-polyoxyalkylenepolyamine adduct. The method includes adding a heparin salt to a periodate solution to give a periodate heparin solution, and adding a polyoxyalkylenepolyamine and a reducing agent to the periodate heparin solution to give a solution of the adduct. Preferably the method further includes dialyzing the solution of the adduct against a solution that includes quaternary ammonium cations.

In another aspect, the present invention includes a method for preparing a medical device. The method includes providing a body of the medical device, applying a composition to coat the body of the medical device, and drying the coated medical device. The composition includes a heparin-polyoxyalkylenepolyamine adduct and an organic solvent In another aspect, the present invention provides a composition including a quaternary ammonium heparin complex, a moisture curable polysiloxane, and an organic solvent.

In another aspect, the present invention provides an object that includes a quaternary ammonium heparin complex and a cured silicone. Preferably the object is a medical device.

In another aspect, the present invention provides a method for preparing a medical device. The method includes providing a body of the medical device, applying a composition to coat the body of the medical device, and drying the coated medical device. The composition includes a quaternary ammonium heparin complex, a moisture curable polysiloxane, and an organic solvent.

Heparin-polyoxyalkylenepolyamine adducts are preferably prepared by treatment of heparin to produce reactive aldehyde molecules on the heparin that may react with amine groups on the polyoxyalkylenepolyamine. Controlled oxidation of heparin molecules to provide a limited number of reactive aldehyde groups on the heparin molecule may be accomplished by treatment with compounds including, for example, nitrous acid or sodium periodate. Preferably, the heparin is treated by controlled oxidation with periodate. Any water soluble periodate may be used, but preferably the periodate is an alkali metal periodate (e.g., sodium periodate). Preferably, the amount of periodate used is sufficient to react with no more than about two of the sugar units in the heparin molecule. The term "sugar molecule" refers to the basic disaccharide residues constituting the structure of the glycosaminoglycan. If the periodate used is sodium periodate and the heparin used is a commercially available injectable form of heparin (e.g., sodium salt with activity of 160 U/milligram), the weight ratio of heparin to periodate should be greater than or equal to about 25:1 in order to react with no more than about two of the sugar units in the heparin molecule. It will be appreciated by those skilled in the art that the amount of periodate required for other periodate compounds and other forms of heparin may be determined by conventional calculations and empirical tests.

The reaction between heparin and periodate preferably takes place in an aqueous buffer solution. Generally, buffers having a pH in a neutral to slightly acidic range of about 4.5 to about 8 may be used, with lower pH (e.g., an acetate buffer at pH 4.5) being preferred if a rapid reaction is desired, while a more neutral pH (e.g., a phosphate buffer at pH 6.88) is preferred for a slower reaction with a longer storage life. With an acetate buffer at pH 4.5, the reaction preferably proceeds for about 3 hours, while with a phosphate buffer at pH 6.88, the reaction preferably proceeds for about 16 hours. If desired, the reacted solution may then be stored at about 5° C. prior to use. The storage stability of the reacted mixture at a neutral pH is preferably about 2 to about 14 days.

The reactive mixture may then be reacted with a polyoxyalkylenepolyamine. Preferably, the reaction mixture is first diluted and the pH adjusted in order to bring the pH of the mixture to a pH that is favorable for the reaction. For example, the reaction mixture may be diluted in an acetate buffer solution (e.g., pH 4.5). A mild reducing agent, for example, sodium cyanoborohydride, may be added to the diluted mixture to effect the reduction of the bonds formed between the reactive aldehyde groups on the oxidized heparin and the amine groups of the polyoxyalkylenepolyamine.

Preferred polyoxyalkylenepolyamines for use in the present invention include, for example, polyoxyethylenepolyamines, polyoxypropylenepolyamines, and poly(oxyethylene-co-oxypropylene)polyamines. Preferably the polyoxyalkylenepolyamines have molecular weights less than or equal to about 5,000 Daltons. Preferably the polyoxyalkylenepolyamines are low viscosity liquids and exhibit low vapor pressure. Preferably the polyoxyalkylenepolyamines are diamines or triamines. Suitable materials are known in the art and include, for example, materials available under the trade designation JEFFAMINE from Huntsman Corp. (Salt Lake City, Utah). Preferred polyoxyalkylenepolyamines include, for example, JEFFAMINE D-230, JEFFAMINE D-400, JEFFAMINE D-2000, JEFFAMINE D-4000, JEFFAMINE ED-600, JEFFAMINE ED-900, JEFFAMINE ED-2001, XTJ-502, JEFFAMINE EDR-148, JEFFAMINE T-403, JEFFAMINE T-3000, and JEFFAMINE T-5000, all available from Huntsman Corp. (Salt Lake City, Utah) or Aldrich Chemical Co. (Milwaukee, Wis.).

A quaternary ammonium heparin-polyoxyalkylenepolyamine adduct complex may be prepared by exchanging cations of the heparin-polyoxyalkylenepolyamine adduct with quaternary ammonium cations. A convenient procedure for the cation exchange is through dialysis using a dialysis membrane. Preferably an aqueous solution of the heparin-polyoxyalkylenepolyamine adduct may be dialyzed against an aqueous solution of a quaternary ammonium halide using a dialysis membrane. For example, an aqueous solution of the heparin-polyoxyalkylenepolyamine adduct may be dialyzed against 0.3% by weight tetrabutylammonium bromide for two days with three changes of solution. Preferred membranes include, for example, benzoylated regenerated cellulose dialysis membranes.

A particularly preferred family of quaternary ammonium compounds useful in the present invention are long chain alkyl quaternary ammonium salts. The salts preferably have 1 to 4 long chain alkyl groups attached to the nitrogen atom, with the alkyl groups preferably having from about 8 to about 30 carbon atoms. The alkyl groups may be like or unlike. The remaining groups are preferably hydrogen, lower alkyl, aryl, alkaryl, and aralkyl groups. The counterion is not critical and is preferably chlorine. These compounds are generally obtained by heating together a tertiary amine and an alkylating agent to thereby produce the quaternary ammonium salt using standard techniques well known to one of ordinary skill in the art. Preferred quaternary ammonium compounds are selected from the group consisting of tridodecylmethylammonium salts, tetradodecylammonium salts, benzalkonium salts, stearyldimethylbenzylammonium salts, and combinations thereof.

A solid quaternary ammonium complex may be isolated from a solution containing the quaternary ammonium complex by methods known in the art. A preferred method of isolating solid quaternary ammonium heparin-polyoxyalkylenepolyamine adduct complexes is freeze drying. For example, an aqueous solution of the quaternary ammonium heparin-polyoxyalkylenepolyamine adduct complex may be freeze dried by cooling the aqueous solution to −80° C. followed by freeze drying under vacuum for 2 days.

Compositions useful for coating may be prepared from organic soluble heparin-polyoxyalkylenepolyamine adducts by dissolving the adduct in an organic solvent. The amount of adduct included in the composition may be selected as desired for particular methods of use and applications. Preferably the composition includes at least about 0.1% by weight adduct and more preferably at least about 1% by weight adduct. Preferably the composition includes at most about 10% by weight adduct and more preferably at most about 3% by weight adduct.

The composition may optionally include polysiloxanes. Preferably the polysiloxanes are capable of being dissolved, suspended, or dispersed in organic solvents. Preferably the polysiloxanes are fluids at room temperature.

Organic solvents useful in compositions of the present invention include solvents that may be removed from a coated layer at drying temperatures of about 25° C. to about 200° C. Useful solvents generally have a boiling point of about 40° C. to about 200° C. Solvents useful in compositions of the present invention include, for example, tetrahydrofuran, acetone, ethanol, isopropanol, methylene chloride, chloroform, hexane, heptane, xylenes, toluene, dioxolane, and N,N-dimethylacetamide. The organic solvent preferably does not include substantial amounts of water.

Preferably the organic solvent includes at most about 10% by weight water and more preferably at most about 2% by weight water.

In another embodiment, compositions useful for coating may be prepared from quaternary ammonium heparin complexes and moisture curable polysiloxanes by dissolving, dispersing, or suspending the components in an organic solvent. The use of moisture curable polysiloxanes may lead to compositions that result in improved properties upon cure compared to the use of other polysiloxanes. For example, the durability of coating prepared from compositions including moisture curable polysiloxanes is preferably improved.

Useful quaternary ammonium heparin complexes include those known in the art (e.g., those available from Polyscience Inc. (Niles, Ill.) or NAMSA (Northwood, Ohio)) and the quaternary ammonium heparin-polyoxyalkylenepolyamine adduct complexes of the present invention. Useful quaternary ammonium heparin complexes include, but are not limited to, benzalkonium heparin-polyoxyalkylenepolyamine adduct complexes, stearyldimethylbenzylammonium heparin-polyoxyalkylenepolyamine adduct complexes, tridodecylmethylammonium heparin-polyoxyalkylenepolyamine adduct complexes, tetradecylammonium heparin-polyoxyalkylenepolyamine adduct complexes, benzalkonium heparin complexes, stearyldimethylbenzylammonium heparin complexes, tridodecylmethylammonium heparin complexes, and tetradodecylammonium heparin complexes. The amount of quaternary ammonium heparin complex included in the composition may be selected as desired for particular methods of use and applications. Preferably the composition includes at least about 0.1% by weight quaternary ammonium heparin complex and more preferably at least about 1% by weight quaternary ammonium heparin complex. Preferably the coating composition includes at most about 10% by weight quaternary ammonium heparin complex and more preferably at most about 3% by weight quaternary ammonium heparin complex.

The moisture curable polysiloxane is preferably capable of being dissolved, suspended, or dispersed in organic solvents. For medical applications, preferred polysiloxanes include, but are not limited to, a medical grade silicone dispersion available under the trade designation MDX 4-4159 from Dow Corning Corp. (Midland, Mich.). According to the Dow Corning Product Information Sheet, Dow Corning MDX-4-4159 is a colorless to slightly hazy liquid aminofunctional medical grade silicone dispersion with 50% by weight active silicone ingredients, and it cures at room temperature between 50–60% relative humidity. Preferably the coating composition includes at least about 0.5% by weight polysiloxane and more preferably at least about 2% by weight polysiloxane. Preferably the coating composition includes at most about 10% by weight polysiloxane and more preferably at most about 5% by weight polysiloxane.

Other components may also be added to coating compositions of the present invention as desired. For example, when the composition is used for coating, components may be added to alter properties of the coating composition including viscosity, color, and reactivity toward the surface to which it will be applied. Components may also be added to alter properties of the resulting coating layer including, for example, coefficient of friction, color, and surface roughness.

Coating methods known in the art may be used to apply the compositions of the present invention to surfaces of a device. Preferably the method is a dip-coating or a spray-coating method. The equipment used will depend on a variety of factors including, for example, the shape and size of the device being coated. For example, when coating elongated medical devices, a dip-coating system may be utilized. The system may have the ability to immerse a device being coated in a container holding the coating composition by movement of either the device, the container, or both. The system may also be capable of withdrawing a device out the coating composition by movement of either the device, the container, or both. The system optionally incorporates equipment that allows accelerated drying of the coated device by methods known in the art including, for example, movement of warm air.

Useful coating parameters (e.g., time, temperature, dipping speed, and withdrawal speed) will depend on factors such as the percent solids of the coating composition, viscosity of the coating composition, and temperature of the coating composition. The temperature of the coating composition may be maintained at any temperature desired, for example, at 25° C.

After the coating is applied, it may be dried by methods known in the art. Suitable drying methods include, but are not limited to, conduction drying, convection drying, hot air impingement, steam treatment, infrared irradiation, ultraviolet irradiation, and microwave irradiation. Preferably the coating is dried by the application of heat. Preferably the coating is dried with air at a temperature of about 25° C. to about 200° C. for about 0.01 second to about 2 hours. After drying, the device may optionally be allowed to cure for a period of about 2 days to about 10 days before use to develop improved coating performance characteristics. If desired, the coated devices may then be packed and sterilized by methods known in the art.

Preferably the coating is applied to result in a dry coating thickness of at least about 0.1 micrometer and preferably at least about 0.5 micrometer. Preferably the coating is applied to result in a dry coating thickness of at most about 100 micrometers and more preferably at most about 10 micrometers.

Preferably the coating and drying methods are selected to provide a uniform coating. Adequate uniformity may be determined by visually inspecting the coated device to ensure that no uncoated surface is exposed. Alternatively, surface uniformity of the coating may be measured by field emission spectrometry (FEM), with a substantially uniform coating showing complete coverage of the surface.

Preferably the coating layer provides antithrombogenic properties for the device to which it is applied. Preferably the antithrombogenic properties are persistent or stable over a period of time, for example, for a period of several hours under high blood flow under in vivo conditions. Preferably the coating layer also has adequate adhesion to the surface of the device, excellent mechanical properties, and suitable electrical properties. Optionally, the coating layer may provide other properties, for example, a lubricious surface.

Compositions of the present invention may be incorporated into devices as desired. Preferably the devices are medical devices. Medical devices in which compositions of the present invention may be incorporated include, but are not limited to, surgical implants, prostheses, and any artificial part or device that replaces or augments a part of a living body or comes into contact with bodily fluids, particularly blood. The substrates may be in any shape or form including tubular, sheet, rod, and articles of proper shape. Various medical devices and equipment usable in accordance with the invention are known in the art. Examples of devices include catheters, suture material, tubing, and fiber membranes. Examples of catheters include central venous catheters, thoracic drain catheters, and angioplasty balloon catheters. Examples of tubing include tubing used in extracorporeal circuitry, for example, whole blood oxygenators. Examples of membranes include polycarbonate membranes, hemodialysis membranes, and membranes used in diagnostic or biosensor devices. Also included are devices used in diagnosis, as well as polyester yarn suture material, for example, polyethylene ribbon and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulas, grafts, implantable pumps, impotence and incontinence implants, intra-occular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, vascular access devices, blood oxygenators, ablation catheters, cannulas, and biopsy needles.

The present invention is illustrated by the following examples. It is to be understood that the particular examples, materials, amounts, and procedures are to be interpreted broadly in accordance with the scope and spirit of the invention as set forth herein.

EXAMPLES

Acetate buffer solution (pH 4.7) was made from acetic acid and sodium acetate, which were obtained from Merck & Co., Inc. (Whitehouse Station, N.J.). Hepes buffer solution, calcium chloride ($CaCl_2$), and isopropyl alcohol (IPA) were obtained from from Merck & Co., Inc. (Whitehouse Station, N.J.). All other reagents were obtained from Aldrich Chemical Co. (Milwaukee, Wis.) unless otherwise specified. Cannulas (03219 14Fr Venous, unless otherwise specified) were obtained from Medtronic DLP (Grand Rapids, Mich.).

Example 1

An organic soluble heparin-polyoxyalkylenepolyamine adduct was synthesized according to the following procedure:
Preparation of Solution A.
Heparin sodium salt (5.5 g, AKZO Nobel, Batch 0008728, 197.5 IU/mg) was reacted with 0.2 g of sodium periodate (Aldrich Chemical Co., Milwaukee, Wis.) in 12 g of 0.02M PBS buffer (pH=6.6, made from disodium hydrogen phosphate and potassium dihydrogen phosphate) for 3 days at room temperature to give a solution of periodate heparin.

Preparation of Solution B.
A mixture of polyoxyalkylenepolyamine (1.1 g) available under the trade designation JEFFAMINE ED 6000 (polyoxyalkylenediamine, Texaco Chemical Co., Bellaire, Tex., CAS No. 65605369) and 0.4 g of sodium cyanoborohydride (Aldrich Chemical Co., Milwaukee, Wis.) in 40 g of 0.2M acetate buffer (pH 4.7) was prepared and added to Solution A and allowed to react at 50° C. for 12 hours.
Preparation of Solution C.
Solution B was dialyzed against a 0.3% by weight aqueous solution of tetrabutylammonium bromide (Aldrich Chemical Co., Milwaukee, Wis.) for 2 days (three changes of solution) using a benzoylated regenerated cellulose dialysis membrane (Aldrich Chemical Co., Milwaukee, Wis.).
Preparation of Adduct D.
Solution C was freeze dried and kept in the freezer at −20° C. to give organic soluble heparin-polyoxyalkylenepolyamine adduct D.
Coating Composition Preparation.
A coating composition was prepared from a mixture of 1.0% by weight Adduct D and 3.0% by weight (1.5% by weight polymer) of a medical grade silicone dispersion available under the trade designation MDX 4-4159 from Dow Corning Corp. (Midland, Mich.) using hexane/water (98:2 by weight) as solvent. According to the Dow Corning Product Information Sheet, Dow Corning MDX-4-4159 is a colorless to slightly hazy liquid aminofunctional medical grade silicone dispersion with 50% by weight active silicone ingredients, and it cures at room temperature between 50–60% relative humidity.
Coating Procedure.
Polyvinyl chloride (PVC) cannulas were coated with the above coating composition by dip-coating the cannula in the coating composition at an immersion speed of about 2.0 centimeters per second (cm/s), a withdrawal speed of about 0.8 cm/s, and a dwell time of about 30 seconds, followed by about 24 hours curing at about room temperature and about 60% relative humidity.

Example 2

A coating composition was prepared from a mixture of 1.2% by weight (0.6% by weight polymer) Dow Corning MDX 4-4159 silicone dispersion and 1.0% by weight heparin benzalkonium complex (H-BAC, NAMSA, Northwood, Ohio) in IPA:hexane (4:1 by weight). A custom made ALIGATR ablation catheter (Medtronic, Fridley, Minn.) was dip or spray-coated with the above prepared coating composition. The coated catheter was cured at room temperature and about 60% humidity for 24 hours.

Tridodecylmethylammonium heparinate (TDMAC-heparin) may also be used instead of H-BAC in the above prepared coating composition. Both H-BAC and TDMAC-heparin are available from Polyscience Inc. (Niles, Ill.) or NAMSA (Northwood, Ohio).

Example 3

PVC cannulas coated as in Example 1 were tested in vitro and the thrombogenicity of the coated devices were compared to that of uncoated devices. Following are descriptions of the tests.
Clotting time.
The inner side of cannulas were exposed to platelet rich plasma ($166 \times 10^9$ platelets/liter) for 15 minutes at 37° C. A small aliquot of 1.0 M $CaCl_2$ was added to start the coagulation reaction. Samples were removed at timed intervals and assayed for thrombin activity. Clotting time coincided with the onset of thrombin generation.

Platelet Adhesion.

The inner side of cannulas were exposed to a citrated platelet rich plasma at 37° C. for 30 minutes. The non-bound platelets were removed by a wash step with Hepes buffer. The material was then exposed to 200 microliters of a 1% by weight aqueous solution of Triton X-100 (available from Sigma-Aldrich, Inc., St. Louis, Mo.) to lyse the platelets. The number of platelets was determined from the lactase dehydrogenase (LDH, an enzyme released from lysed platelets) activity in the lysate. The data in Table 2 illustrate that coated cannulas were less thrombogenic than uncoated cannulas as clotting time was prolonged and platelet adhesion was reduced.

TABLE 2

In-Vitro Thrombogenicity

|  | Clotting time (seconds) | Platelet adhesion $10^3$ cells/cm$^2$ |
| --- | --- | --- |
| Coated cannula | 1016 | 104 |
| Uncoated cannula | 687 | 338 |

Example 4

Polypropylene (PP) films (ICI Inc., Belgium) were coated according to the procedure described in Example 2. The content of the polymer component (MDX-4-4159) in the coating was varied between 0.0% by weight (wt.) and 0.9% by weight. Comparison of the coated samples was done by staining with Toluidine Blue (Aldrich Chemical Co., Milwaukee, Wis.) before and after extensive washing of samples in a fluid available under the trade designation Plasma-Lyte from Baxter Healthcare Corp. (Deerfield, Ill.). The dye uptake is believed to be proportional to the quantity of heparin remaining in the sample. Visual observation indicated that after about 4 hours of washing, practically no dye uptake was seen for samples having 0.0% by weight of MDX 4-4159 silicone dispersion, while the dye uptake was still very high, even after 68 hours of washing, for the samples having 0.9% by weight of MDX 4-4159 silicone dispersion. The MDX 4-4159 silicone dispersion component added even at very low percentages to the coating permits sustained release of heparin from the coating layer. This observation was confirmed quantitatively by measuring the release of heparin using a calorimetric assay as shown in Table 3.

TABLE 3

Heparin Release after Rinse with Plasma-Lyte Solution

| Sample Description | | Heparin Release in mU/cm$^2$ after: | | | |
| --- | --- | --- | --- | --- | --- |
| MDX 4-4159 (% by wt.) | Heparin (% by wt.) | 1$^{st}$ Rinse (0.5 hr.) | 2$^{nd}$ Rinse (1 hr.) | 3$^{rd}$ Rinse (2 hr.) | 4$^{th}$ Rinse (24 hr.) |
| 0.0 | 0.3 | 42 | 10 | 9 | 4 |
| 0.1 | 0.3 | 11 | 6 | 12 | 9 |
| 0.0 | 0.9 | 75 | 56 | 37 | 25 |
| 0.9 | 0.9 | 45 | 43 | 36 | 50 |

Example 5

Polypropylene films were coated as in Example 4. After staining with Toluidine Blue, the stained films were dried in air. After drying, the adhesion of the coating was tested by applying to the sample and then removing a pressure sensitive adhesive tape available under the trade designation SCOTCH Transparent Film Tape 681 from 3M (St. Paul, Minn.). The tape was applied with a force of 1 Newton per square centimeter for 1 minute. The tape was then removed by pulling at a 90 degree angle from the surface at a speed of 1 centimeter per second. When no MDX 4-4159 silicone dispersion was added to the coating, the tape was able to remove nearly all the coating layer. When the concentration of the MDX 4-4159 silicone dispersion in the coating fluid was 0.3% by weight, no stained coating was observed being pulled from the coated sample. This test indicates an improvement in the adhesion and/or mechanical stability of the coating observed when MDX 4-4159 silicone dispersion is added to the coating composition.

Example 6

A custom made ablation catheter available under the trade designation ALIGATR from Medtronic, Inc. (Fridley, Minn.) was coated as described in Example 2. No measurable difference in the flexibility of the catheter was detected using standard testing tools.

Example 7

Custom made ablation catheters available under the trade designation ALIGATR from Medtronic, Inc. (Fridley, Minn.) were coated as described in the Example 2. One catheter was coated by dip-coating and the other was coated by spray-coating. Ablation catheters (uncoated and coated) were tested under identical test conditions (0.5 U/milliliter heparin concentration in fresh human blood, 37° C. blood temperature, flow rate=50 milliliters/minute). The results for "ALIGATR" catheters are illustrated by FIGS. 1 to 3.

FIG. 1 is a photograph of an uncoated catheter after being exposed to blood for 30 minutes, followed by rinsing with Plasma-Lyte A. Coagulated blood was clearly visible covering the surface of the catheter.

Figure 2:
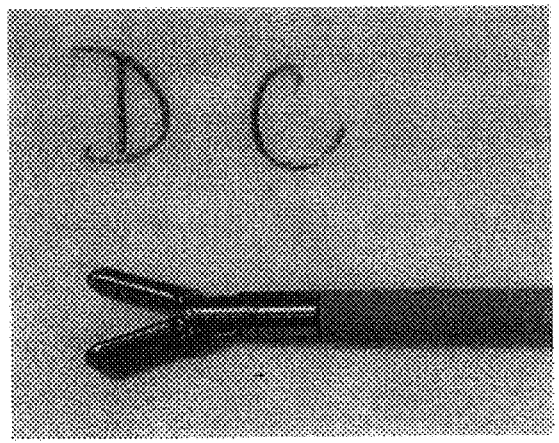
FIG. 2 is a photograph of a catheter, which was dip-coated with a coating composition of the present invention, after being exposed to blood for 30 minutes, followed by rinsing with Plasma-Lyte A.

FIG. 2 is a photograph of a catheter, which was dip-coated with a coating composition as in Example 2, after being exposed to blood for 30 minutes, followed by rinsing with Plasma-Lyte A. The surface of the catheter appeared to be clean with no visible signs of blood coagulation.

Figure 3:
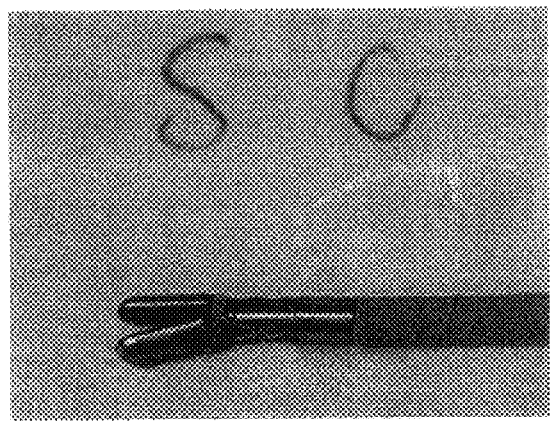
FIG. 3 is a photograph of a catheter, which was spray-coated with a coating composition of the present invention, after being exposed to blood exposure for 30 minutes, followed by rinsing with Plasma-Lyte A.

FIG. 3 is a photograph of a catheter, which was spray-coated with a coating composition as in Example 2, after being exposed to blood for 30 minutes, followed by rinsing with Plasma-Lyte A. The surface of the catheter appeared to be clean with no visible signs of blood coagulation.

Example 8

A custom made ablation catheter available under the trade designation ALIGATR from Medtronic, Inc. (Fridley, Minn.) was coated as described in Example 2. The coated catheter was then inserted into the left atrium of a dog. Saline was permitted to flow through the tip. Several ablations were performed at different locations. Following each ablation, the catheter was removed and examined for thrombus. Thrombus was not observed anywhere during the first several burns. After the fourth ablation, a tiny amount of charring was noted on one of the Z-wires. Good lesions were observed during autopsy. A clear formation of thrombus was observed on the uncoated catheter in a similar experiment.

The complete disclosure of all patents, patent applications, and publications, and electronically available material cited herein are incorporated by reference.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to antithrombogenic medical devices. The present invention is also not limited to medical devices per se, but may find further applications such as, for example, devices having protective coatings. The present invention further includes within its scope methods of making and using heparin compositions as described hereinabove.

What is claimed is:

1. A heparin-polyoxyalkylenepolyamine adduct.

2. The adduct of claim 1 wherein the adduct is organic soluble.

3. The adduct of claim 1 wherein the adduct is a quaternary ammonium complex.

4. The adduct of claim 1 wherein the polyoxyalkylenepolyamine is selected from the group consisting of polyoxyethylenepolyamine, polyoxypropylenepolyamine, poly(oxyethylene-co-oxypropylene)polyamine, and combinations thereof.

5. A composition comprising a heparin-polyoxyalkylenepolyamine adduct, a polysiloxane, and an organic solvent.

6. The composition of claim 5 wherein the adduct is organic soluble.

7. A method for preparing a heparin-polyoxyalkylenepolyamine adduct comprising:

adding a heparin salt to a periodate solution to give a periodate heparin solution; and adding a polyoxyalkylenepolyamine and a reducing agent to the periodate heparin solution to give a solution of the adduct.

8. The method of claim 7 further comprising dialyzing the solution of the adduct against a solution comprising quaternary ammonium cations.

9. A composition comprising:

a quaternary ammonium heparin complex;

a moisture curable polysiloxane; and an organic solvent.

10. The composition of claim 9 wherein the quaternary ammonium heparin complex is selected from the group consisting of benzalkonium heparin complexes, stearyldimethylbenzylammonium heparin complexes, tridodecylmethylammonium heparin complexes; tetradodecylammonium heparin complexes, benzalkonium heparin-polyoxyalkylenepolyamine adduct complexes, stearyldimethylbenzylammonium heparin-polyoxyalkylenepolyamine adduct complexes, tridodecylmethylammonium heparin-polyoxyalkylenepolyamine adduct complexes, tetradodecylammonium heparin-polyoxyalkylenepolyamine adduct complexes, and combinations thereof.

* * * * *

UNITED STATES PATENT AND TRADEMARK OFFICE
CERTIFICATE OF CORRECTION

| | | |
|---|---|---|
| PATENT NO. | : 6,630,460 B2 | |
| APPLICATION NO. | : 09/779536 | |
| DATED | : October 7, 2003 | |
| INVENTOR(S) | : Edouard Koullick | |

It is certified that error appears in the above-identified patent and that said Letters Patent is hereby corrected as shown below:

Title page, item (75) Inventor: Edouard Koulik… should read… Edouard Koullick

Signed and Sealed this
Eighth Day of May, 2012

David J. Kappos
*Director of the United States Patent and Trademark Office*